United States Patent
Mikami et al.

[11] Patent Number: 5,723,643
[45] Date of Patent: Mar. 3, 1998

[54] METHOD FOR THE PREPARATION OF ACRYLOXY- OR METHACRYLOXY-FUNCTIONAL ORGANOSILICON COMPOUNDS

[75] Inventors: Ryuzo Mikami; Tadashi Okawa, both of Chiba Prefecture, Japan

[73] Assignee: Dow Corning Toray Silicone Co., Ltd., Tokyo, Japan

[21] Appl. No.: 834,201

[22] Filed: Apr. 15, 1997

[30] Foreign Application Priority Data

Apr. 26, 1996 [JP] Japan ................................. 8-131432

[51] Int. Cl.$^6$ ................................................. C07F 7/08
[52] U.S. Cl. ................................................. 556/440; 556/441
[58] Field of Search ............................... 556/440, 441

[56] References Cited

U.S. PATENT DOCUMENTS

| | | | |
|---|---|---|---|
| 5,103,032 | 4/1992 | Turner et al. | 556/401 |
| 5,145,979 | 9/1992 | Takatsuna et al. | 556/440 |
| 5,262,555 | 11/1993 | Okawa et al. | 556/440 |
| 5,493,039 | 2/1996 | Okawa et al. | 556/440 |

FOREIGN PATENT DOCUMENTS

| | | |
|---|---|---|
| 5-301881 | 11/1993 | Japan . |
| 7-25907 | 1/1995 | Japan . |

*Primary Examiner*—Paul F. Shaver
*Attorney, Agent, or Firm*—William F. Boley

[57] ABSTRACT

A method to make high-purity acryloxy- or methacryloxy-functional organosilicon compounds in high yields by inhibiting gelation of the reaction product during preparation. The method comprises (A) reacting an acrylate or methacrylate ester of an alcohol comprising an aliphatically unsaturated bond or a phenol comprising an aliphatically unsaturated bond with a (B) SiH-functional silicon compound in the presence of (C) a hydrosilylation reaction catalyst and (D) a polymerization inhibitor described by formula

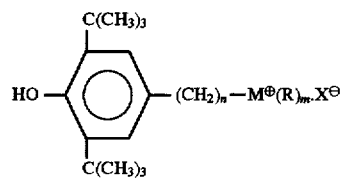

where n is 0 or 1; M is an atom selected from the group consisting of N, P, As, Sb, O, S, Se, Sn, and I; R is a monovalent hydrocarbon group or hydrogen atom; m is 1, 2, or 3; and X is a conjugate base of an organic acid or inorganic acid.

The present method can further comprise distillation of the reaction mixture resulting from the reaction of component (A) and (B) in the presence of component (D).

15 Claims, No Drawings

METHOD FOR THE PREPARATION OF ACRYLOXY- OR METHACRYLOXY-FUNCTIONAL ORGANOSILICON COMPOUNDS

BACKGROUND OF INVENTION

This invention relates to methods for the preparation of organosilicon compounds that contain the acryloxy or methacryloxy group (hereinafter abbreviated as (meth)acryloxy-functional organosilicon compounds). More particularly, this invention relates to an efficient method for the high-yield synthesis of very pure (meth)acryloxy-functional organosilicon compounds in which gelation of the reaction product during the production process is inhibited.

(Meth)acryloxy-functional organosilicon compounds readily react with radical-polymerizable monomers such as methyl methacrylate and styrene and as a consequence are used as starting materials for copolymers deriving from these monomers and as modifiers for polymers obtained from these monomers.

(Meth)acryloxy-functional organosilicon compounds can be prepared by an addition reaction between a SiH-functional halosilane and the corresponding acrylate or methacrylate ester of an alcohol or phenol that contains an aliphatically unsaturated bond. The desired (meth)acryloxy-functional organosilicon compound is then isolated from the resulting mixture by distillation. Refer in this regard to, for example, Japanese Patent Application Kokai Number Hei 5-301881 (301,881/1993). However, this addition reaction and isolation by distillation has been encumbered by severe difficulties because compounds of this type readily polymerize upon heating and as a result can become highly polymerized during the reaction and distillation stages. This polymerization makes it quite difficult to obtain high-purity (meth)acryloxy-functional organosilicon compounds in high yields. Because of this problem it is necessary to run the addition reaction of these methods at temperatures at which this thermal polymerization will not occur. However, this type of temperature control is quite difficult and the reaction product often ends up becoming highly polymerized and gelled anyway.

The addition of a hindered phenol, amine compound, or quinone compound to the reaction system has also been proposed as a tactic for inhibiting the strong polymerization and gelation of acrylic-functional organosilicon compounds. For example, Japanese Patent Application Kokai Number Hei 7-25907 (25,907/1995) describes a substantial improvement in thermal stability by the addition of 2,6-di-tert-butyl-4-hydroxymethylphenol to a crude mixture prepared from γ-methacryloxypropyltrichlorosilane and methanol whose main component is γ-methacryloxypropyltrimethoxysilane. This inhibitor, however, essentially cannot provide a complete inhibition of gelation during the addition reaction between a SiH-functional halosilane and the acrylate or methacrylate ester of an aliphatically unsaturated alcohol or phenol. In addition, Japanese Patent Application Kokai Number Hei 5-186478 (186,478/1993) has proposed the use of N,N-dialkylaminomethylenephenol as a polymerization inhibitor. This inhibitor performs relatively well in terms of inhibiting the polymerization of acrylic-functional silanes and halosilanes. However, it acts as a catalyst poison for the platinum catalysts used in the preparation of these silanes by the above-described addition reaction, with the result that large amounts of platinum catalyst must be employed in order to complete the reaction.

The inventors have already proposed a method in which metal halide is added as a polymerization inhibitor to the distillative purification of the reaction mixture afforded by the aforementioned addition reaction (Japanese Patent Application Kokai Number Hei 5-271248 (271,248/1993)). This method provides the desired (meth)acryloxy-functional organosilicon compound in high yields without the occurrence of gelation during separation by distillation. Unfortunately, since this type of metal halide is easily reduced by silicon-bonded hydrogen to give either a lower valent metal halide or the metal itself, this method cannot be applied to the inhibition of polymerization or gelation during the addition reaction.

As a result of extensive investigations directed to solving the problems described above, the inventors have discovered that a special class of compounds provides a substantial stabilization of the reaction mixture during the addition reaction of the acrylate or methacrylate ester of an aliphatically unsaturated alcohol or phenol. These compounds as a result act to inhibit gelation during the addition reaction. Moreover, these compounds exert their effects without inhibiting the addition reaction. The object of the present invention is to provide a high-yield method for the preparation of high-purity (meth)acryloxy-functional organosilicon compounds in which gelation of the reaction mixture is inhibited.

SUMMARY OF INVENTION

A method to make high-purity acryloxy- or methacryloxy-functional organosilicon compounds in high yields by inhibiting gelation of the reaction product during preparation. The method comprises (A) reacting an acrylate or methacrylate ester of an alcohol comprising an aliphatically unsaturated bond or a phenol comprising an aliphatically unsaturated bond with a (B) SiH-functional silicon compound in the presence of (C) a hydrosilylation reaction catalyst and (D) a polymerization inhibitor described by formula

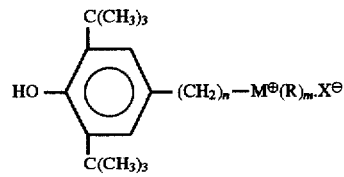

where n is 0 or 1; M is an atom selected from the group consisting of N, P, As, Sb, O, S, Se, Sn, and I; R is a monovalent hydrocarbon group or hydrogen atom; m is 1, 2, or 3; and X is a conjugate base of an organic acid or inorganic acid.

The present method can further comprise distillation of the reaction mixture resulting from the reaction of component (A) and (B) in the presence of component (D).

DESCRIPTION OF INVENTION

The present invention is a method for the preparation of (meth)acryloxy-functional organosilicon compounds. The method comprises (A) reacting an acrylate or methacrylate ester of an alcohol comprising an aliphatically unsaturated bond or a phenol comprising an aliphatically unsaturated bond with a (B) SiH-functional silicon compound in the presence of (C) a hydrosilylation reaction catalyst and (D) a polymerization inhibitor described by formula

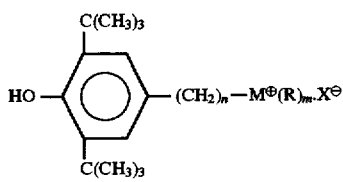

where n is 0 or 1; M is an atom selected from the group consisting of N, P, As, Sb, O, S, Se, Sn, and I; R is a monovalent hydrocarbon group or hydrogen atom; m is 1, 2, or 3; and X is a conjugate base of an organic acid or inorganic acid.

The present method can further comprise distillation of the reaction mixture resulting from the reaction of component (A) and (B) in the presence of component (D). The presence of component (D) during the distillation process prevents polymerization of the (meth)acryloxy-functional organosilicon product during the distillation process.

Component (A) used in the present method is the acrylate or methacrylate ester of an alcohol that contains an aliphatically unsaturated bond or a phenol that contains an aliphatically unsaturated bond. The acrylate esters are exemplified by allyl acrylate, hexenyl acrylate, allyloxyethyl acrylate, and 4-vinylphenyl acrylate. The methacrylate esters are exemplified by allyl methacrylate, hexenyl methacrylate, allyloxyethyl methacrylate, and 4-vinylphenyl methacrylate.

No specific restrictions apply to the SiH-functional silicon compound (B) other than that the boiling point of the product afforded by the addition reaction should fall in a temperature range at which distillation can be carried out. The organosilicon compound is exemplified by trichlorosilane, methyldichlorosilane, dimethylchlorosilane, trimethoxysilane, methyldimethoxysilane, dimethylmethoxysilane, pentamethyldisiloxane, and 1,1,3,3-tetramethyldisiloxane.

The hydrosilylation reaction catalyst employed as component (C) in the present method preferably comprises a transition metal from Group VIII of the Periodic Table, among which platinum catalysts are the most preferred. These platinum catalysts are exemplified by alcohol solutions of chloroplatinic acid, platinum-olefin complexes, and complexes of platinum and vinyl-functional siloxane.

The polymerization inhibitor (D) used in the present method is described by formula

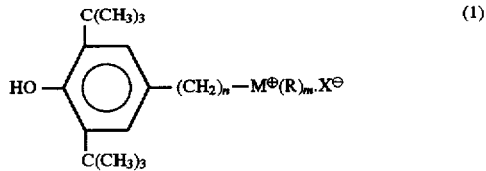

(1)

where n is 0 or 1; M is an atom selected from the group consisting of N, P, As, Sb, O, S, Se, Sn, and I; R is a monovalent hydrocarbon group or hydrogen atom; m is 1, 2, or 3; and X is a conjugate base of an organic acid or inorganic acid.

In formula (1), R is the hydrogen atom or a monovalent hydrocarbon group, and examples of the latter include alkyl groups such as methyl, ethyl, and propyl; alkenyl groups such as vinyl, allyl, and butenyl; aryl groups such as phenyl, tolyl, and xylyl; and aralkyl groups such as phenylethyl and diphenylmethyl. Methyl and hydrogen are preferred for R.

In formula (1), M is an atom selected from the group consisting of N, P, As, Sb, O, S, Se, Sn, and I. While m in general can have a value of 1, 2, or 3, m will be 3 when M is N, P, As, or Sb; 2 when M is O, S, Se, or Sn; and 1 when M is I.

In formula (1), X refers to the conjugate base of an organic or inorganic acid and is exemplified by halogen ions, which are the conjugate bases of hydrogen halides such as hydrogen chloride and hydrogen bromide; by the conjugate bases of carboxylic acids such as acetic acid, propionic acid, and acrylic acid; and by the conjugate bases of sulfuric acid, sulfonic acid, and phosphoric acid.

Polymerization inhibitors useful as component (D) are exemplified by compounds with the following molecular structures, in which R and X are as defined above.

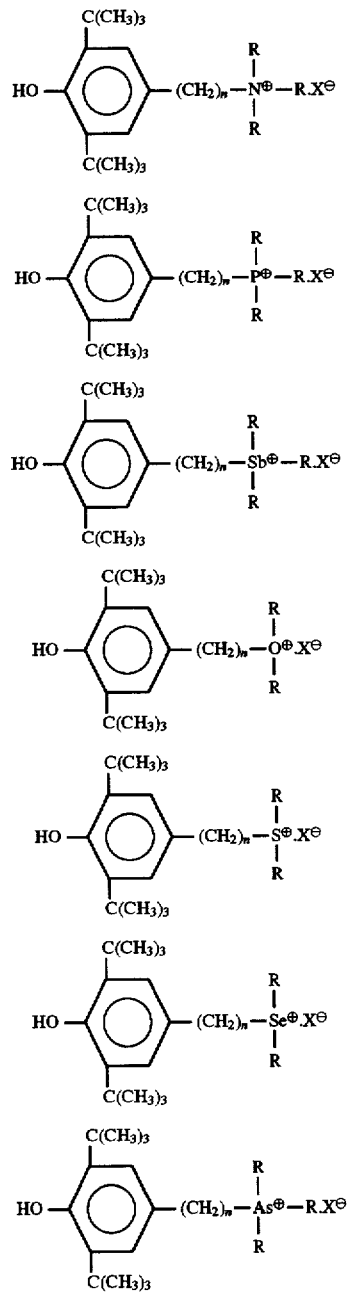

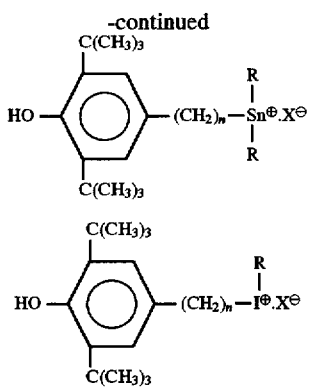

A preferred polymerization inhibitor is selected from the group having the following chemical structures were R is the hydrogen atom or a monovalent hydrocarbon group as described above.

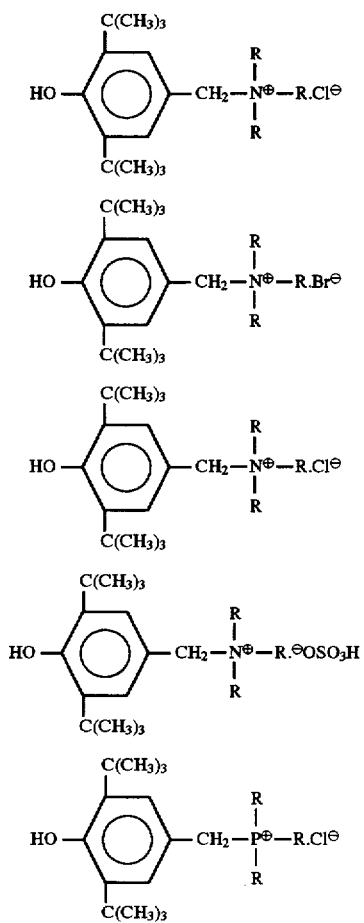

The present polymerization inhibitors are easily synthesized by well-known methods in which an organic acid or inorganic acid or organic halide is reacted with the corresponding substituted or unsubstituted phenol-containing Lewis base.

The present method comprises reacting components (A) and (B) in the presence of a catalysis (component (C)) and polymerization inhibitor (component (D)). The present method can further comprises distillation of the resulting reaction mixture comprising component (D). Component (D) is preferably added to the present method at from 0.001 to 10 weight %, based on the total weight of components (A) to (C).

The present method can be run with or without solvent. Useable solvents include aromatic hydrocarbons such as benzene, toluene, and xylene; aliphatic hydrocarbons such as hexane and heptane; ethers such as tetrahydrofuran and diether ether; ketones such as acetone and methyl ethyl ketone; and esters such as ethyl acetate and butyl acetate.

The present method can be run at room temperature, but is preferably run at temperatures of at least 30° C. in order to obtain good reaction rates. Since (meth)acryloxy-functional organosilicon compounds readily polymerize and gel at high temperatures, the reaction temperature preferably does not exceed 100° C., more preferably the reaction temperature is in the range from 30° C. to 100° C., and even more preferably the reaction temperature is in the range from 50° C. to 95° C.

Distillation can be run directly after completion of this addition reaction without further intervention, but the hindered phenols, amine compounds, quinones, and oxygen already known as radical polymerization inhibitors can also be added and used in combination with the polymerization inhibitor according to the present invention. Moreover, the addition of a metal halide as proposed by the inventors in Japanese Patent Application Kokai Number Hei 2-71248 will provide additional stabilization of the reaction system and make possible the high-yield recovery of the target (meth)acryloxy-functional organosilicon compound by distillation in a vacuum without the production of a gel by-product. These metal halides are specifically exemplified by the chlorides, bromides, and iodides of chromium, cobalt, nickel, germanium, zinc, tin, mercury, copper, iron, palladium, tungsten, and silver, among which cupric chloride is most preferred. The general range of addition for the metal halide is from 0.01 to 10 weight % of the overall weight of the reaction mixture, but its addition is not specifically restricted as long as its addition is capable of inhibiting polymerization.

The presence of polymerization inhibitor (D) in the addition reaction between (A) the acrylate or methacrylate ester of an aliphatically unsaturated alcohol of phenol and (B) SiH-functional organosilicon compound catalyzed by (C) hydrosilylation catalyst, or in the distillation of the reaction mixture inhibits the polymerization or gelation of component (A) and product (meth)acryloxy-functional organosilicon compounds.

The invention will be explained in greater detail below through working examples, but the invention is not limited to these examples.

SYNTHESIS EXAMPLE 1

A mixture comprising 20 g (76 millimoles) 2,6-di-tert-butyl-4-dimethylaminomethylphenol, 15.1 g (168 millimoles) trimethylsilanol, and 140 mL toluene was formed. Then, 9.2 g (84 millimoles) trimethylchlorosilane were added dropwise to this mixture forming a white precipitate. After stirring for 30 minutes at room temperature, the white precipitate was filtered off, washed with toluene, and dried under vacuum at 80° C. for 3 hours to give 22.5 g of the white precipitate. Analysis of the white precipitate by nuclear magnetic resonance analysis (NMR) and infrared absorption analysis (IR) confirmed it to be 3,5-di-tert-butyl-4-hydroxyphenylmethyldimethylammonium chloride as described by formula:

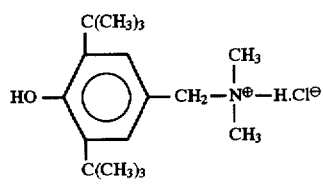

EXAMPLE 1

100 g (794 millimoles) Allyl methacrylate and 0.1 g of the 3,5-di-tert-butyl-4-hydroxyphenylmethyldimethylammonium chloride whose synthesis is described in Synthesis Example 1 were introduced into a stirrer-equipped four-neck flask. A platinum/1,3-divinyltetramethyldisiloxane complex was then added to the flask in sufficient quantity to give 20 ppm platinum metal relative to the weight of the allyl methacrylate. After heating to 90° C. under a nitrogen blanket, a small amount of dimethylchlorosilane was added dropwise. After confirmation of initiation of the reaction, 68.2 g (722 millimoles) of dimethylchlorosilane were added dropwise while maintaining the reaction temperature at 85° C. to 95° C. by cooling. Stirring was carried out for 30 minutes at 80° C. after completion of the addition. 0.1 g 2,6-Di-tert-butyl-4-methylphenol was added followed by distillation at 5 mm Hg. The fraction distillating off at 92° C. to 105° C. was collected. This fraction, identified as 3-methacryloxypropyldimethylchlorosilane, weighed 126.1 g (yield=79%).

EXAMPLE 2

2,000 g (15.9 moles) Allyl methacrylate and 3.0 g of the 3,5-di-tert-butyl-4-hydroxyphenylmethyldimethylammonium chloride whose synthesis is described in Synthesis Example 1 were introduced into a stirrer-equipped four-neck flask. A platinum/1,3-divinyltetramethyldisiloxane complex was then added to the flask in sufficient quantity to give 20 ppm platinum metal relative to the weight of the allyl methacrylate. After heating to 80° C. while bubbling in nitrogen containing 2% oxygen at the rate of 0.1 L/minute, a small amount of dimethylchlorosilane was added dropwise. After confirmation of initiation of the reaction, 1,364 g (14.4 moles) dimethylchlorosilane were added dropwise while maintaining the reaction temperature at 75° C. to 80° C. by cooling. Stirring was carried out for 1 hour at 75° C. after completion of the addition. 30 g of cupric chloride and 2 g of 2,6-di-tert-butyl-4-methylphenol were added to the resulting reaction mixture followed by distillation at 5 mm Hg. The fraction distilling of at 90° C. to 110° C. was collected. This fraction, identified as 3-methacryloxypropyldimethylchlorosilane, weighed 2,323 g (yield=73%). The residue was 180 g of a low-viscosity liquid.

COMPARATIVE EXAMPLE 1

An addition reaction was run as in Example 2, but in this case using 0.8 g phenothiazine and 8 g hydroquinone monomethyl ether as polymerization inhibitors instead of the 3.0 g 3,5-di-tert-butyl-4-hydroxyphenylmethyldimethylammonium chloride. The reaction was also run under air in this comparative example. The reaction mixture lost its fluidity and gelled by the time the addition of the dimethylchlorosilane to the reaction was completed.

COMPARATIVE EXAMPLE 2

50 g (397 millimoles) Allyl methacrylate was placed in a stirrer-equipped four-neck flask and dry air was bubbled through the allyl methacrylate for 30 minutes. This was followed by the admixture under a nitrogen blanket of 0.1 g phenothiazine and sufficient platinum/1,3-divinyltetramethyldisiloxane complex to provide 20 ppm platinum metal relative to the weight of the allyl methacrylate. The mixture was heated to 75° C. and a small amount of dimethylchlorosilane was added dropwise. After initiation of the reaction had been confirmed, 37.5 g (397 millimoles) dimethylchlorosilane were added dropwise while the reaction temperature was maintained at 65° C. to 75° C. by cooling. Stirring was continued at 60° C. for 1 hour after the completion of addition. 0.88 g Triethylamine hydrochloride was then added to this reaction mixture and the mixture distilled at 5 mm Hg. The obtained fraction, identified as 3-methacryloxypropyldimethylchlorosilane, weighed 31.8 g (yield=36%). The residue had lost its fluidity and had gelled.

I claim:

1. A method for preparation of acryloxy- or methacryloxy-functional organosilicon compounds comprising (A) reacting an acrylate or methacrylate ester of an alcohol comprising an aliphatically unsaturated bond or a phenol comprising an aliphatically unsaturated bond with a (B) SiH-functional silicon compound in the presence of (C) a hydrosilylation reaction catalyst and (D) a polymerization inhibitor described by formula

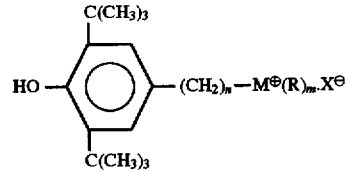

where n is 0 or 1; M is an atom selected from the group consisting of N, P, As, Sb, O, S, Se, Sn, and I; R is a monovalent hydrocarbon group or hydrogen atom; m is 1, 2, or 3; and X is a conjugate base of an organic acid or inorganic acid.

2. A method according to claim 1, where component (A) comprises an acylate ester selected from the group consisting of allyl acrylate, hexenyl acrylate, allyloxyethyl acrylate, and 4-vinylphenyl acrylate.

3. A method according to claim 1, where component (A) comprises a methacrylate ester selected from the group consisting of allyl methacrylate, hexenyl methacrylate, allyloxyethyl methacrylate, and 4-vinylphenyl methacrylate.

4. A method according to claim 1, where the SiH-functional silicon compound is selected from the group consisting of trichlorosilane, methyldichlorosilane, dimethylchlorosilane, trimethoxysilane, methyldimethoxysilane, dimethylmethoxysilane, pentamethyldisiloxane, and 1,1,3,3-tetramethyldisiloxane.

5. A method according to claim 1, where the hydrosilylation catalyst is a platinum catalyst.

6. A method according to claim 1, where the hydrosilylation catalyst is a platinum catalyst selected from the group consisting of an alcohol solution of chloroplatinic acid, platinum-olefin complexes, and complexes of platinum and vinyl-functional siloxane.

7. A method according to claim 1, where R is selected from the group consisting of methyl and hydrogen.

8. A method according to claim 1, where X is the conjugate base of a hydrogen halide.

9. A method according to claim 1, where X is the conjugate base of a hydrogen halide selected from the group consisting of hydrogen chloride and hydrogen bromide.

10. A method according to claim 1, where X is the conjugate base of a carboxylic acid.

11. A method according to claim 1, where X is the conjugate base of an inorganic acid selected from the group consisting of sulfuric acid, sulfonic acid, and phosphoric acid.

12. A method according to claim 1, where the polymerization inhibitor is selected from the group described by formulas

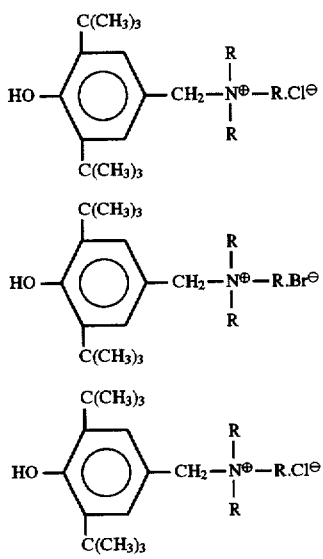

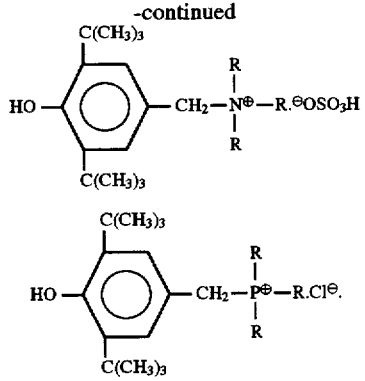

13. A method according to claim 1, where the acrylate is allyl acrylate and the SiH-functional silicon compound is dimethylchlorosilane.

14. A method according to claim 1 further comprising distillating the reaction product of component (A) and (B) in the presence of component (D) thereby recovering a acryloxy- or methacryloxy-functional organosilicon compound.

15. A method according to claim 1, where the polymerization inhibitor is described by formula

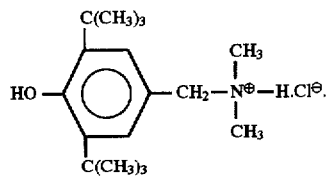

* * * * *